(12) United States Patent
Sato

(10) Patent No.: US 10,052,024 B2
(45) Date of Patent: Aug. 21, 2018

(54) BIOMETRIC DEVICE, BIOMETRIC METHOD, PROGRAM, AND RECORDING MEDIUM

(75) Inventor: Hideo Sato, Tokyo (JP)

(73) Assignee: Sony Corporation (JP)

( * ) Notice: Subject to any disclaimer, the term of this patent is extended or adjusted under 35 U.S.C. 154(b) by 730 days.

(21) Appl. No.: 14/357,001

(22) PCT Filed: Aug. 22, 2012

(86) PCT No.: PCT/JP2012/071221
§ 371 (c)(1),
(2), (4) Date: May 8, 2014

(87) PCT Pub. No.: WO2013/073244
PCT Pub. Date: May 23, 2013

(65) Prior Publication Data
US 2014/0296719 A1 Oct. 2, 2014

(30) Foreign Application Priority Data
Nov. 16, 2011 (JP) .................................. 2011-250996

(51) Int. Cl.
| *A61B 5/1455* | (2006.01) |
| *A61B 5/00* | (2006.01) |
| *G01N 21/64* | (2006.01) |
| *G01N 21/359* | (2014.01) |
| *G01N 21/49* | (2006.01) |

(52) U.S. Cl.
CPC .......... *A61B 5/0071* (2013.01); *A61B 5/1455* (2013.01); *G01N 21/645* (2013.01); *G01N 21/6486* (2013.01); *G01N 21/359* (2013.01); *G01N 21/49* (2013.01); *G01N 2021/6463* (2013.01)

(58) Field of Classification Search
CPC ................ A61B 5/0071; A61B 5/1455; G01N 2021/6463; G01N 21/645; G01N 21/6486; G01N 21/359; G01N 21/49
See application file for complete search history.

(56) References Cited

U.S. PATENT DOCUMENTS

| 8,130,383 B2 | 3/2012 | Suzuki | |
| 8,649,568 B2 | 2/2014 | Sato | |
| 8,788,021 B1 * | 7/2014 | Flusberg | ............. A61B 5/0059 356/318 |

(Continued)

FOREIGN PATENT DOCUMENTS

| JP | 2-240545 | 9/1990 |
| JP | 5-203563 A | 8/1993 |

(Continued)

OTHER PUBLICATIONS

International Search Report dated Nov. 27, 2012.

*Primary Examiner* — Vani Gupta
(74) *Attorney, Agent, or Firm* — Lerner, David, Littenberg, Krumholz & Metlik, LLP

(57) ABSTRACT

Provided is a biometric device which may include a light source unit configured to irradiate an organism with inspection light, a light-collection unit arranged facing a region on a surface of the organism and configured to spatially-integrally collect output light emitted from the region in accordance with the inspection light, and a light-reception unit configured to receive the collected output light.

12 Claims, 14 Drawing Sheets

(56) References Cited

U.S. PATENT DOCUMENTS

2009/0218514 A1  9/2009  Klunder et al.
2011/0164249 A1  7/2011  Innami et al.

FOREIGN PATENT DOCUMENTS

| | | |
|---|---|---|
| JP | 11-037938 | 2/1999 |
| JP | 2002-000586 A | 1/2002 |
| JP | 2004-344668 A | 12/2004 |
| JP | 2008-523383 A | 7/2008 |
| JP | 2009-026142 A | 2/2009 |
| JP | 2011-097986 A | 5/2011 |
| WO | 2007-037253 A1 | 4/2007 |

* cited by examiner

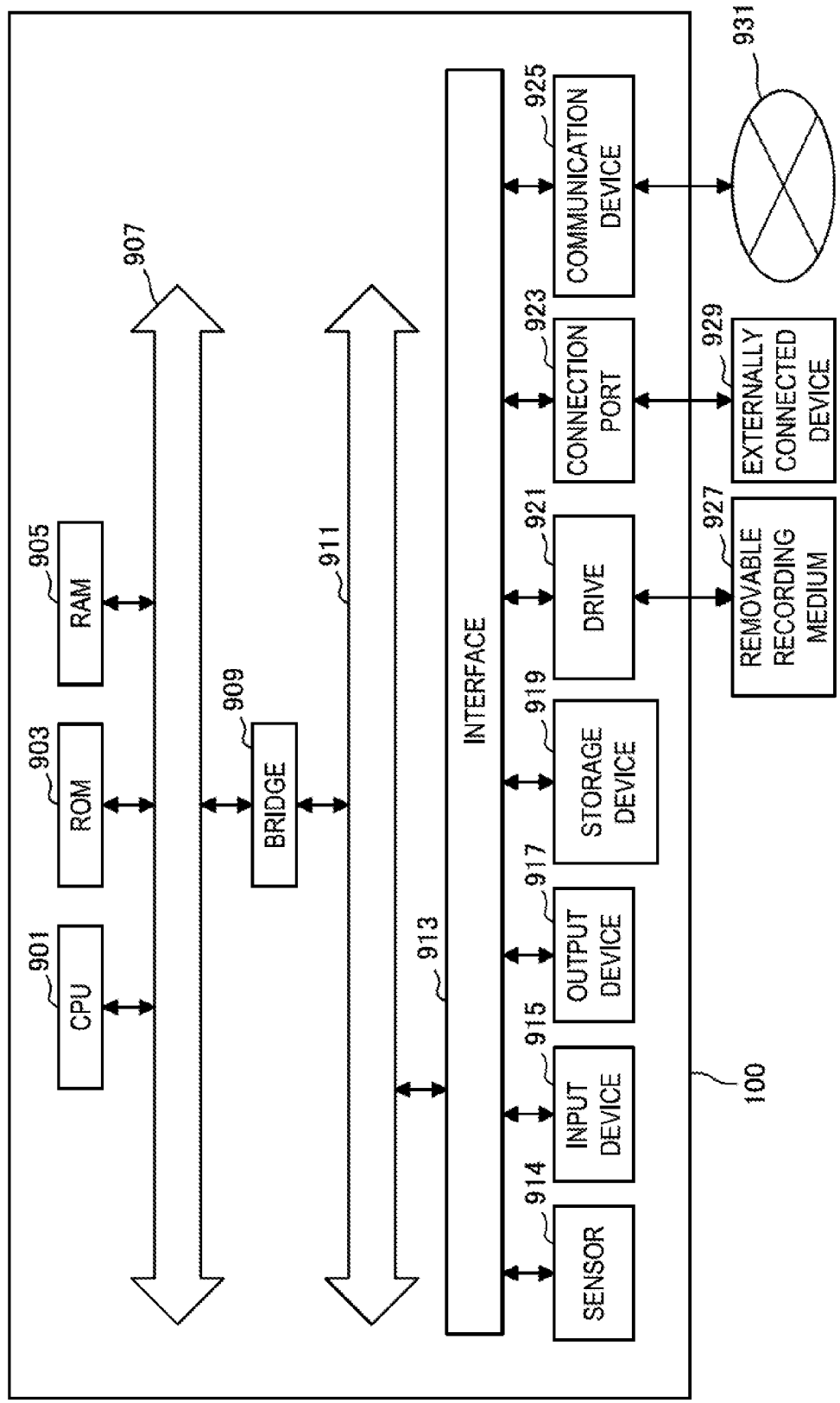

BIOMETRIC DEVICE, BIOMETRIC METHOD, PROGRAM, AND RECORDING MEDIUM

CROSS-REFERENCE TO RELATED APPLICATION

The present application is a national phase entry under 35 U.S.C. §371 of International Application No. PCT/JP2012/071221 filed Aug. 22, 2012, published on May 23, 2013 as WO 2013/073244 A1, which claims priority from Japanese Patent Application No. JP 2011-250996, filed in the Japanese Patent Office on Nov. 16, 2011.

TECHNICAL FIELD

The present disclosure relates to a biometric device, a biometric method, a program, and a recording medium.

BACKGROUND ART

In recent years, technologies for non-invasively carrying out biometric measurements using spectroscopy such as Raman spectroscopy or near infrared spectroscopy, or fluorescence spectroscopy and the like, for example, have been developed. These technologies are utilized in an inspection of a substance in a subcutaneous tissue or detection of a pulse wave signal from an artery. In such biometric technologies, when a substance which lies subcutaneously in minute amounts is measured, for example, light emitted in a wide area on a surface of an organism needs to be collected to ensure precision of measurements. In this case, it was general to expand an area which can receive light by setting a large distance from the surface of the organism to a light-reception unit, or use a large-size light-reception device as described in Patent Literature 1, for example.

CITATION LIST

Patent Literature

Patent Literature 1: JP 2009-026142A

SUMMARY OF INVENTION

Technical Problem

However, if a large distance is set from a surface of an organism to a light-reception unit, measurement results are affected by light in a surrounding environment. In addition, if a large-size light-reception device is used, a device configuration becomes extensive, and furthermore arrangement or shape of the light-reception unit is restricted.

Hence, in the present disclosure, a new and improved biometric device, biometric method, program and recording medium which can implement spectroscopic measurements of receiving light from a wide area on a surface of an organism in a freer manner and with high precision are proposed.

Solution to Problem

According to the present disclosure, there is provided a biometric device including a light source unit configured to irradiate an organism with inspection light, a light-collection unit arranged facing a region on a surface of the organism and configured to spatially-integrally collect output light emitted from the region in accordance with the inspection light, and a light-reception unit configured to receive the collected output light.

According to the present disclosure, there is provided a biometric method including irradiating an organism with inspection light, spatially-integrally collecting output light emitted from a region on a surface of the organism in accordance with the inspection light, and receiving the collected output light.

According to the present disclosure, there is provided a program for causing a computer included in a biometric device including a light source unit, a light-collection unit, and a light-reception unit to implement a function of controlling the light source unit, and a function of controlling the light-reception unit, the light source unit being configured to irradiate an organism with inspection light, the light-collection unit being arranged facing a region on a surface of the organism and being configured to spatially-integrally collect output light emitted from the region in accordance with the inspection light, the light-reception unit being configured to receive the collected output light.

According to the present disclosure, there is provided a computer-readable recording medium having a program recorded thereon, the program causing a computer included in a biometric device including a light source unit, a light-collection unit, and a light-reception unit to implement a function of controlling the light source unit, and a function of controlling the light-reception unit, the light source unit being configured to irradiate an organism with inspection light, the light-collection unit being arranged facing a region on a surface of the organism and being configured to spatially-integrally collect output light emitted from the region in accordance with the inspection light, and the light-reception unit being configured to receive the collected output light.

According to the present disclosure, there is provided a biometric device including a light source unit configured to irradiate an organism with inspection light, a light-collection unit arranged facing a region on a surface of the organism and configured to spatially-integrally collect output light emitted from the region in accordance with the inspection light, and a light-reception unit configured to receive the collected output light. The light-collection unit is divided to collect the output light for each of a plurality of sub-regions into which the region is divided. The light-reception unit receives the output light in a time division manner, the output light each being collected by the divided light-collection units.

According to the configurations of the present disclosure as described above, the output light emitted from a predetermined region on the surface of the organism is spatially-integrally collected by the light-collection unit and received by the light-reception unit. Therefore, while light can be received from a wide area on the surface of the organism, there is no need to set a large distance from the surface of the organism to the light-reception unit or make the light-reception unit large-size. In addition, since the light-collection unit may be composed of a more flexible material than the light-reception unit, it is easy to set arrangement or shape of a biometric device freely.

Advantageous Effects of Invention

According to the present disclosure as described above, spectroscopic measurements for collecting light from a wide area on a surface of an organism can be implemented in a freer manner and with high precision.

BRIEF DESCRIPTION OF DRAWINGS

FIG. 14 is a block diagram for illustrating a hardware configuration of an information processor.

DESCRIPTION OF EMBODIMENTS

Hereinafter, preferred embodiments of the present invention will be described in detail with reference to the appended drawings. Note that, in this specification and the drawings, elements that have substantially the same function and structure are denoted with the same reference signs, and repeated explanation is omitted.

Note that descriptions will be given in the following order:
1. Description of related art
2. Embodiments of the present disclosure
   2-1. First embodiment
   2-2. Second embodiment
   2-3. Third embodiment
   2-4. Fourth embodiment
   2-5. Fifth embodiment
   2-6. Sixth embodiment
3. Supplement

1. DESCRIPTION OF RELATED ART

Figure 1:
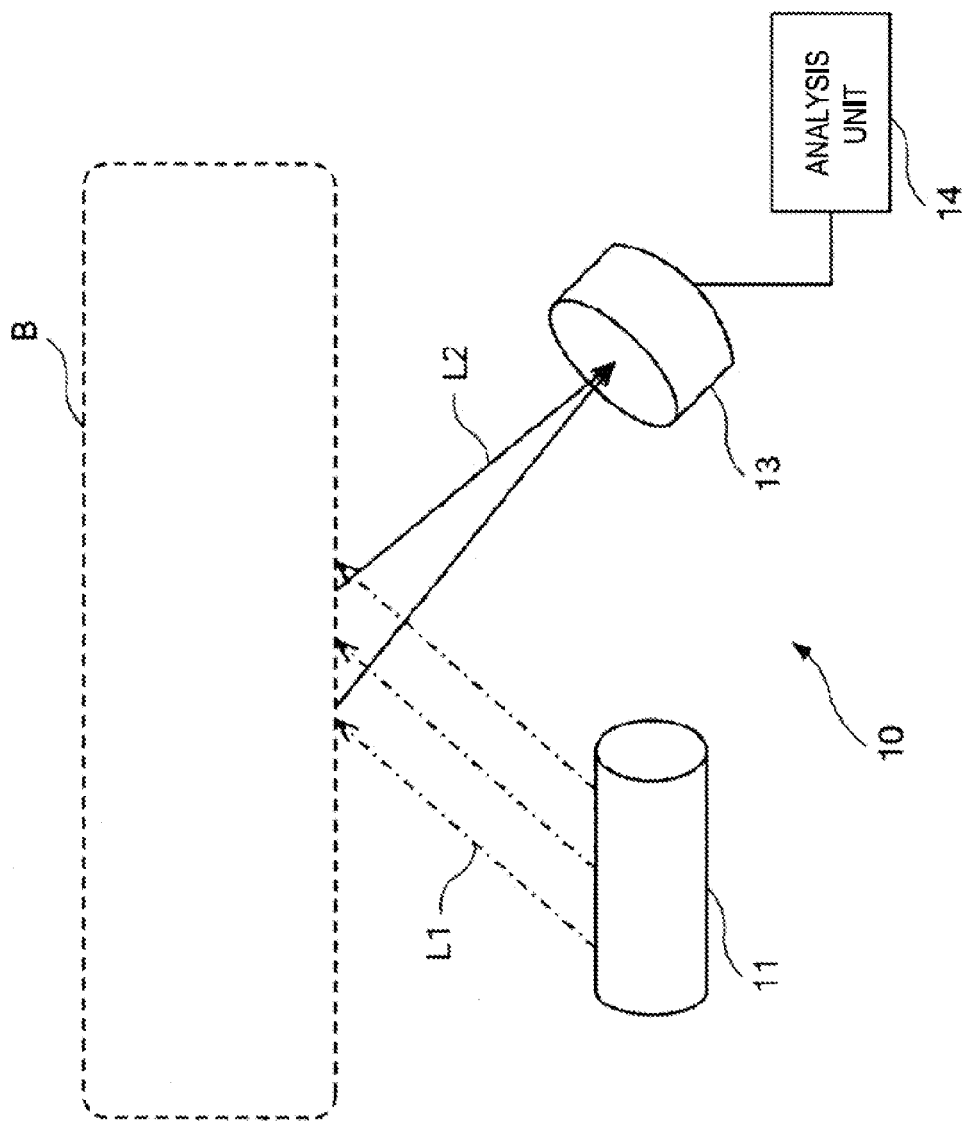
FIG. 1 is an illustration showing a configuration of a biometric device according to related art of embodiments of the present disclosure.

First, the art related to embodiments of the present disclosure will be described with reference to FIG. 1. FIG. 1 is an illustration showing a configuration of a biometric device according to the related art of the embodiments of the present disclosure.

With reference to FIG. 1, a biometric device 10 includes a light source unit 11, a light-reception unit 13, and an analysis unit 14. The biometric device 10 is a biometric device which performs biometric measurements using spectroscopy. The light source unit 11 irradiates a measurement target part on a surface of an organism B with inspection light L1. Output light L2 is emitted from the organism B in accordance with the inspection light L1 which enters the organism B. The light-reception unit 13 receives the output light L2. The analysis unit 14 analyzes the output light L2 received by the light-reception unit 13.

In the aforementioned biometric device 10, a certain distance is set between the light-reception unit 13 and the organism B so that the light-reception unit 13 can receive the output light L2 from a wide area on the surface of the organism B. Therefore, measurement results may be affected by light in a surrounding environment.

In addition, as another example for receiving the output light L2 from a wide area on the surface of the organism B, a large-size light-reception device may be used as the light-reception unit. In this case, however, a device configuration becomes extensive, and furthermore arrangement or shape of the light-reception unit is restricted. Moreover, a large-size light-reception device is generally expensive.

Hereinafter, some of the embodiments of the present disclosure will be described. Some advantages of these embodiments will be understood more easily through a comparison with the biometric device according to the related art described above.

2. EMBODIMENTS OF THE PRESENT DISCLOSURE

2-1. First Embodiment

Figure 2:
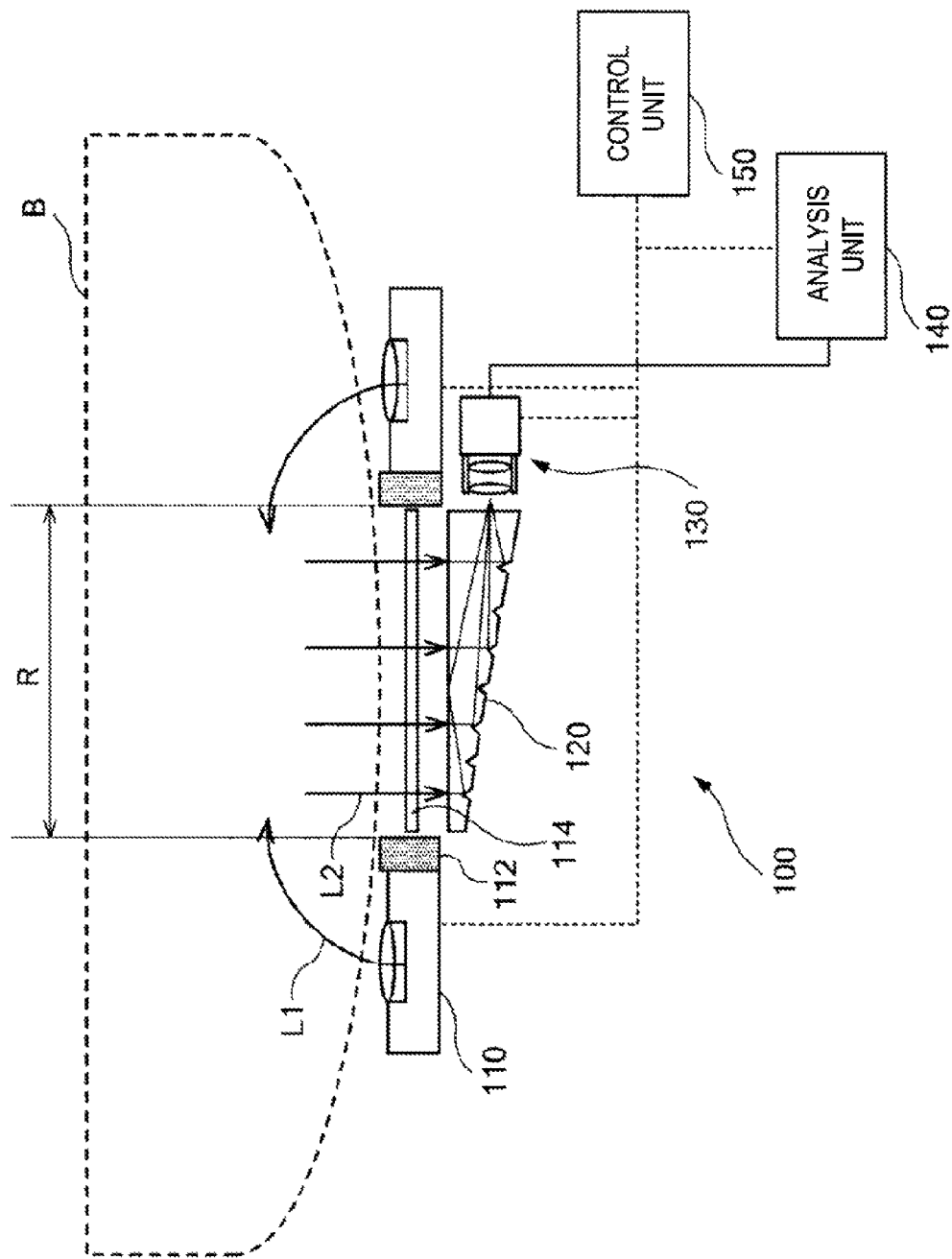
FIG. 2 is an illustration showing a configuration of a biometric device according to a first embodiment of the present disclosure.
Figure 3:
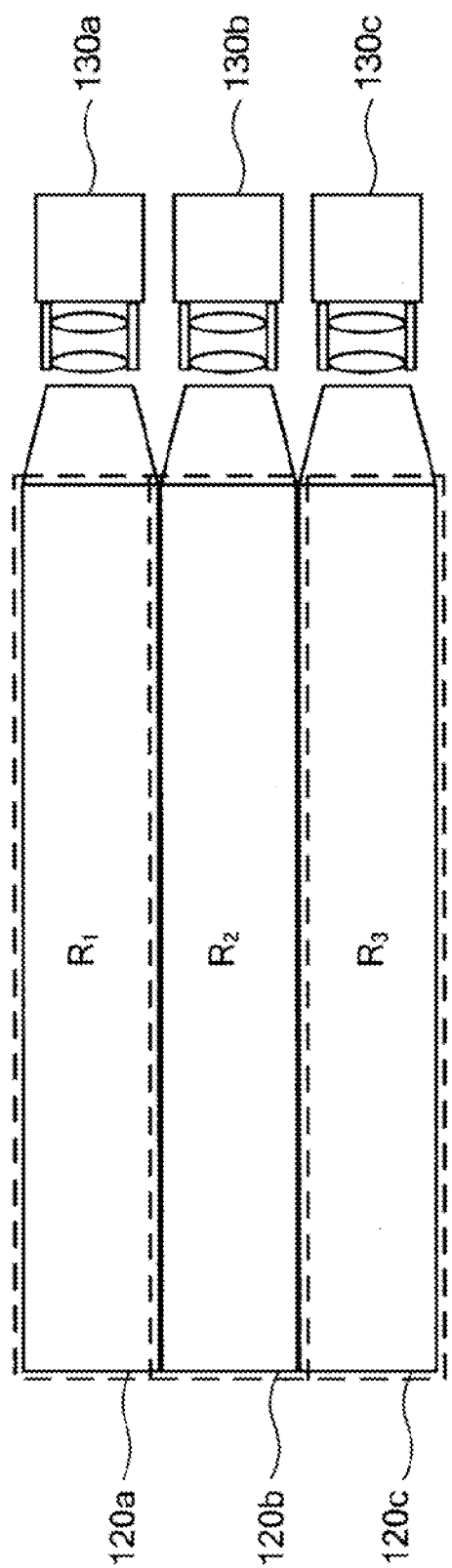
FIG. 3 is an illustration showing an example of dividing a microprism array in the first embodiment of the present disclosure.
Figure 4:
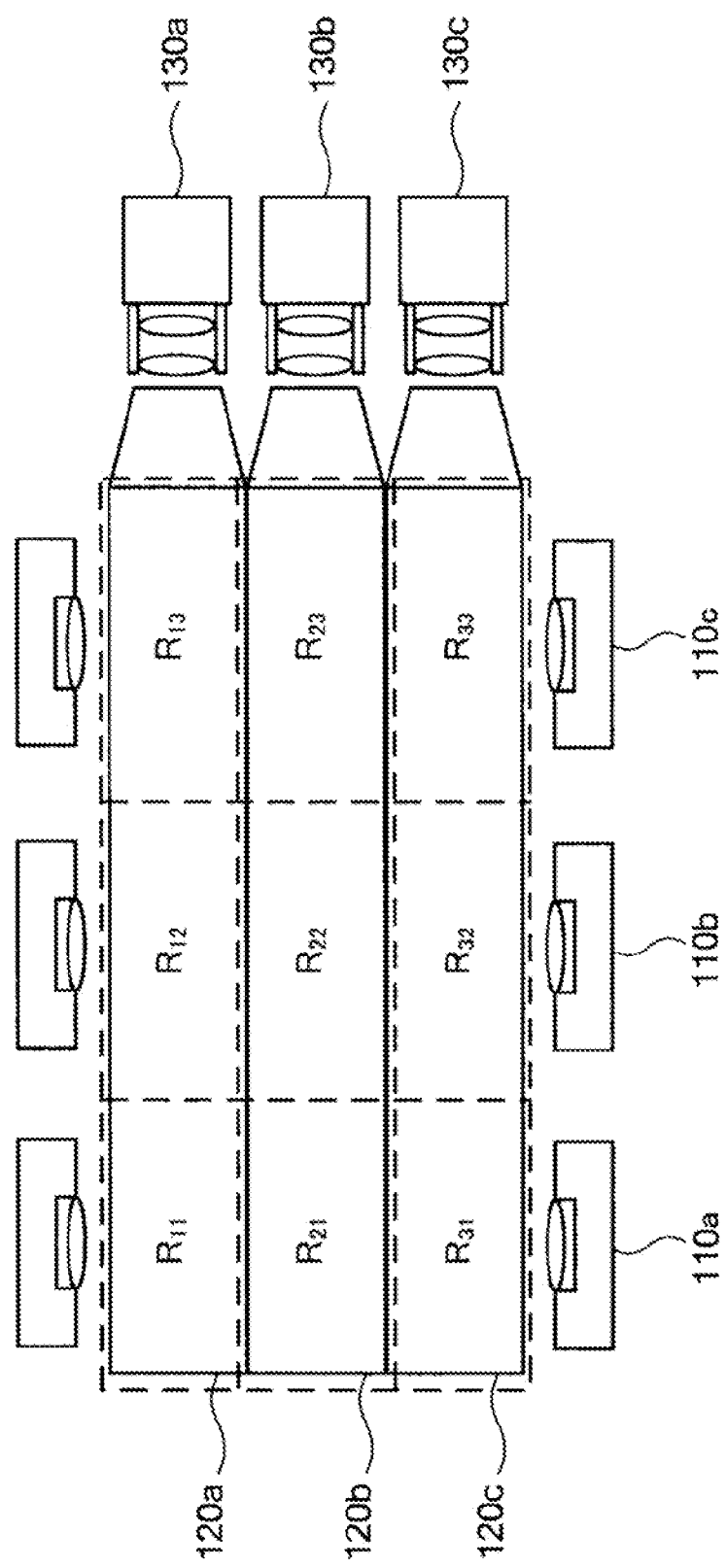
FIG. 4 is an illustration showing an example of further dividing a light source unit in the first embodiment of the present disclosure.
Figure 5:
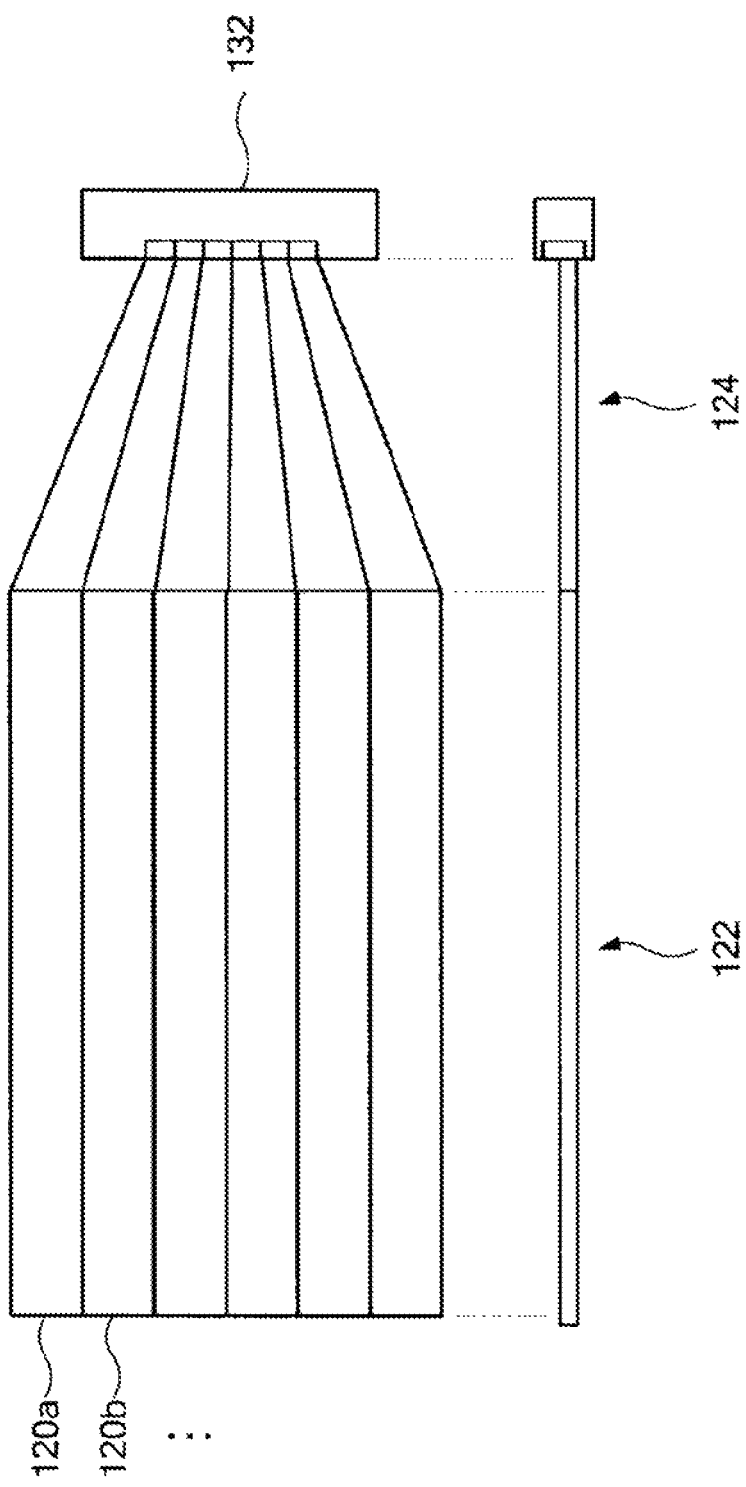
FIG. 5 is an illustration showing an example of using a line sensor for a light-reception unit in the first embodiment of the present disclosure.

First, a first embodiment of the present disclosure will be described with reference to FIG. 2 to FIG. 5. FIG. 2 is an illustration showing a configuration of a biometric device according to the first embodiment of the present disclosure. FIG. 3 is an illustration showing an example of dividing a region in the first embodiment of the present disclosure. FIG. 4 is an illustration showing an example of further dividing the region in the first embodiment of the present invention. FIG. 5 is an illustration showing an example of using a line sensor for a light-reception unit in the first embodiment of the present disclosure.

With reference to FIG. 2, a biometric device 100 includes a light source unit 110, a light shield 112, a filter 114, a microprism array 120, a light-reception unit 130, an analysis unit 140, and a control unit 150. The biometric device 100 is a biometric device which performs biometric measurements using spectroscopy.

The light source unit 110 irradiates an organism B with inspection light L1. Here, the inspection light L1 is excitation light for placing a body substance of the organism B in an excited state and causing it to emit fluorescence light as output light L2. In this case, near-ultraviolet rays or visible rays of short wavelength, for example, are used as the inspection light L1, which is not limited thereto, though, and light of any wavelength can be used as far as it is light that can place a substance in the body into an excited state. In addition, the inspection light L1 may be light such as near infrared rays which are scattered and absorbed within the organism B and emitted as the output light L2. As the light source unit 110, for example, a light emitting diode (LED: Light Emitting Diode) or a small-size laser and the like is used.

The microprism array 120 is a light-collection unit which is arranged facing a region R on a surface of the organism B and spatially-integrally collects the output light L2 emitted from the region R in accordance with the inspection light L1. Spatial-integral light collection herein means converging the output light L2 emitted from the region R into a region smaller than the region R, by reflecting or refracting the output light L2. In the shown example, the microprism array 120 converges the output light L2 emitted from the region R in a cross section direction into one spot and guides it to the light-reception unit 130. As another example, the microprism array 120 may converge the output light L2 in a cross section direction into a plurality of spots and guide it to the light-reception unit 130.

The light-reception unit 130 receives the output light L2 collected by the microprism array 120. The light-reception unit 130 converts the output light L2 received with a photo detector (PD: Photo Detector) and the like into an electric signal, supplies it to the analysis unit 140. Here, the light-reception unit 130 may include a two-dimensional spectroscope to acquire data of the output light L2 as a two-dimensional image having a wavelength axis and a visual field axis.

In this embodiment, as described above, a light-reception area of the light-reception unit 130 can be made smaller than the region R by spatial-integral collection of the output light L2 with the microprism array 120. Therefore, if the region R is large, for example, a large-size light-reception unit may not be used as the light-reception unit 130, which can simplify the device configuration. Since the microprism array 120 may be formed of a lightweight and flexible material such as resin and the like, for example, a degree of freedom in arrangement or shape is high. In addition, since both the surface of the organism B can be in proximity to or in contact with the microprism array 120, and the microprism array 120 can be in proximity to or in contact with the light-reception unit 130, influence of light in a surrounding environment on measurement results can be reduced.

The light shield 112 is arranged between the light source unit 110 and the microprism array 120. The light shield 112 prevents the inspection light L1 applied from the light source unit 110, for example, from entering the side of the microprism array 120 immediately or after being reflected on the surface of the organism B. This reduces the inspection light L1 which is received by the light-reception unit 130 and affects analysis results of the output light L2 and improves an S/N (Signal/Noise) ratio, which can consequently improve precision of the analysis of the output light L2.

The filter 114 is an optical filter arranged between the organism B and the microprism array 120. The filter 114 is a narrowband bandpass filter that is provided when wavelength of the inspection light L1 differs from that of the output light L2, for example, and lets light of the wavelength of the output light L2 pass while not letting light of wavelength of the inspection light L1 pass. In this case, for example, the inspection light L1 scattered within the organism B can be prevented from reaching the microprism array 120. Similar to the case of the light shield 112, this can improve precision of the analysis of the output light L2.

The analysis unit 140 is implemented by a computer having a CPU (Central Processing Unit), a RAM (Random Access Memory), a ROM (Read Only Memory) and the like, for example. The analysis unit 140 analyzes the data of the output light L2 acquired from the light-reception unit 130. By way of example, the analysis unit 140 analyzes spectrum or intensity of the output light L2 which is fluorescence light. This enables quantification of a body substance of the organism B emitting fluorescence light. Note that the analysis unit 140 may be a part of the biometric device 100 or an external device to be connected to the biometric device 100. In addition, data of the output light L2 generated by the light-reception unit 130 is stored in a removable storage medium, which is then removed from the biometric device 100 and connected to other device having an analysis unit 140, so that the data of the output light L2 may be analyzed.

The control unit 150 is implemented by a computer having a CPU, a RAM, a ROM and the like, for example. The control unit 150 controls operation of each unit of the aforementioned biometric device 100. For example, the control unit 150 controls operation of the aforementioned light source unit 110 and the light-reception unit 130.

FIG. 3 shows an example of dividing the region R in this embodiment. FIG. 3 is a top view of the microprism array 120 and the light-reception unit 130 shown in FIG. 2 when they are viewed from the above. The figure shows sub-regions $R_1$ to $R_3$ into which the region R is divided, segments 120a to 120c of the microprism array 120 which are divided corresponding to the sub-regions $R_1$ to $R_3$, and light-reception units 130a to 130c for individually receiving the output light 2 collected by the segments 120a to 120c respectively.

Here, for example, by alternatively receiving the output light L2, the light-reception units 130a to 130c can individually receive the output light L2 collected by the sub-regions $R_1$ to $R_3$ respectively. The light-reception units 130a to 130c may receive the output light L2 sequentially in chronological order. Note that the microprism array 120 is physically divided into the segments 120a to 120c, for example. In this case, a light shield for preventing leakage of light from contiguous segments may be provided on boundaries of the segments 120a to 120c. In addition, the microprism array 120 may be functionally divided and used as the segments 120a to 120c.

On the one hand, FIG. 4 shows an example of further dividing the region R in the example of FIG. 3. Here, if a direction in which the region R is divided into the sub-regions $R_1$ to $R_3$ in the example of FIG. 3 is made a first direction, the region R is further divided in a second direction, which differs from the first direction, in the example of FIG. 4. More specifically, in the example of FIG. 4, the region R is divided in the first direction and the second direction which is orthogonal thereto, respectively, and sub-regions $R_{11}$ to $R_{33}$ are formed in a matrix shape. Here, the sub-regions $R_{11}$, $R_{12}$, $R_{13}$ correspond to the sub-region $R_1$ in the example of FIG. 3, the sub-regions $R_{21}$, $R_{22}$, $R_{23}$ similarly correspond to the sub-region $R_2$, and the sub-regions $R_{31}$, $R_{32}$, $R_{33}$ similarly correspond to the sub-region $R_3$.

Here, in the shown example, division of the region R in the second direction is implemented through setting of a plurality of sub-irradiated regions into which the region R is divided in the second direction and arrangement of light source units 110a to 110c corresponding to respective sub-irradiated regions. The sub-irradiated regions corresponding to the light source unit 110a are regions consisting of the sub-regions $R_{11}$, $R_{21}$, $R_{31}$, the sub-irradiated regions corresponding to the light source unit 110b are regions consisting of the sub-regions $R_{12}$, $R_{22}$, $R_{32}$, and the sub-irradiated regions corresponding to the light source unit 110c are regions composed of $R_{13}$, $R_{23}$, $R_{33}$.

Here, for example, the light-reception units 130a to 130c alternatively receive the output light L2, similar to the example of FIG. 3. The light-reception units 130a to 130c may also receive the output light L2 sequentially in chronological order. This can switch light reception from the sub-regions $R_{11}$, $R_{21}$, $R_{31}$, light reception from the sub-regions $R_{12}$, $R_{22}$, $R_{32}$, and light reception from the sub-regions $R_{13}$, $R_{23}$, $R_{33}$.

Furthermore, the light source units 110a to 110c alternatively apply the inspection light L1. The light source units 110a to 110c may apply the inspection light L1 sequentially in chronological order. This can switch irradiation of the sub-regions $R_{11}$, $R_{21}$, $R_{31}$, irradiation of the sub-regions $R_{12}$, $R_{22}$, $R_{32}$, and irradiation of the sub-regions $R_{13}$, $R_{23}$, $R_{33}$.

Thus, combining switching of the light-reception unit 130 and irradiation of the light source unit 110 enables any region of the sub-regions $R_{11}$ to $R_{33}$ to be irradiated with the inspection light L1 and to receive the output light L2.

A configuration whereby a region is divided and output light L2 is locally collected, as described above, is effective in a case in which a pulse in the wrist (radial artery) is taken, for example. A site of the wrist is effective as an inspection site of the pulse, as can be seen from the fact that it is used in a medical examination. However, when the inspection site is away from the radial artery, amplitude of a pulse wave becomes small to the extent that detection is difficult. Here, as described below, if a microprism array is arranged in an annular casing of a biometric device, and a region around the wrist is divided to measure the pulse wave as in the aforementioned example, a user can automatically select a region where wavelength of an optimal pulse wave can be obtained even if he/she has not mastered the operation.

FIG. 5 shows an example of using a line sensor 132 for the light-reception unit 130. FIG. 5 is a top view of the microprism array 120 and the light-reception unit 130 shown in FIG. 2 when they are viewed from the above. In the example shown, the microprism array 120 is divided into segments 120a, 120b, . . . which receive output light L2 for each of sub-regions into which a region R is divided. In addition, the microprism array 120 has a light-reception portion 122 and a connecting portion 124. The light-reception portion 122 is a portion which faces the region R and receives the output light L2. The connecting portion 124 is a portion which guides the output light L2 collected by the light-collecting portion 122 to the line sensor 132. Use of the line sensor 132 for the light-reception unit 130 can downsize a biometric device 100, for example.

Note that the number of divisions of the region R in respective examples described above is an example, and that the region R may be divided into any number both in the first and the second directions.

2-2. Second Embodiment

Figure 6:
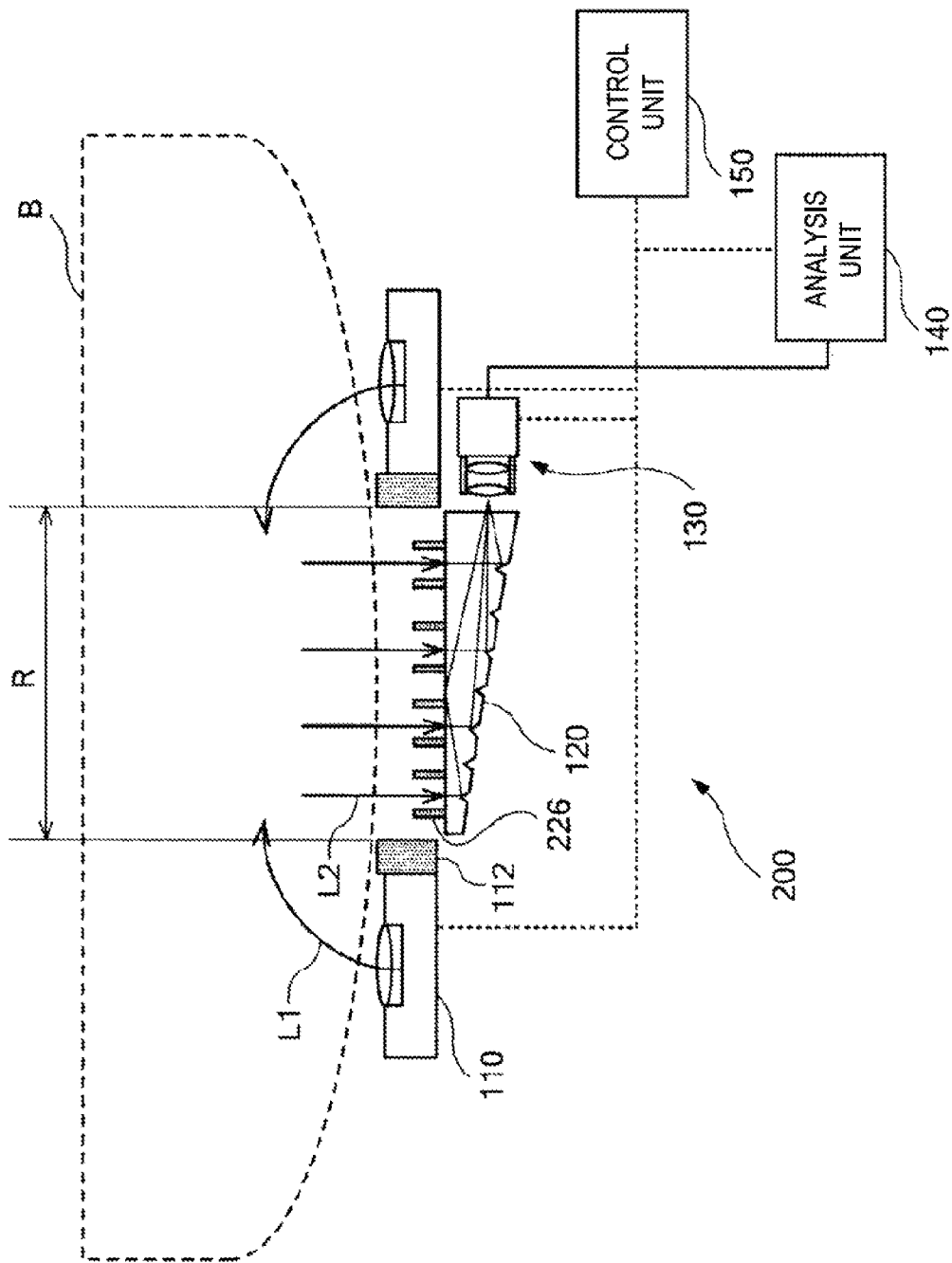
FIG. 6 is an illustration showing a configuration of a biometric device according to a second embodiment of the present disclosure.

A second embodiment of the present disclosure will be described hereinafter, with reference to FIG. 6. FIG. 6 is an illustration showing a configuration of a biometric device according the second embodiment of the present disclosure.

With reference to FIG. 6, a biometric device 200 includes a light source unit 110, a light shield 112, a microprism array 120, a light-collection unit light shield 226, a light-reception unit 130, an analysis unit 140, and a control unit 150. Note that of the aforementioned components, those other than the light-collection unit light shield 226 can have a similar configuration to the first embodiment described above, and thus a detailed description will be omitted.

The light-collecting light shield 226 is an optical member for limiting directionality of light entering the microprism array 120. For example, the light-collecting light shield 226 selectively lets output light L2 in a direction perpendicular to an organism B pass and enter the light-reception unit 130. This can prevent inspection light L1 which leaks from the light source units 110, for example, from mixing into light incident to the microprism array 120.

As in this embodiment, if fluorescence spectroscopy is used, for example, provision of an optical member which limits directionality of the output light L2 entering the microprism array 120 can prevent excitation light scattered in a part other than a body substance subject to measurement or fluorescence light emitted by a body substance not subject to measurement from mixing into output light L2 subject to measurement, thereby enabling improvement of precision in measurements using the output light L2.

2-3. Third Embodiment

Figure 7:
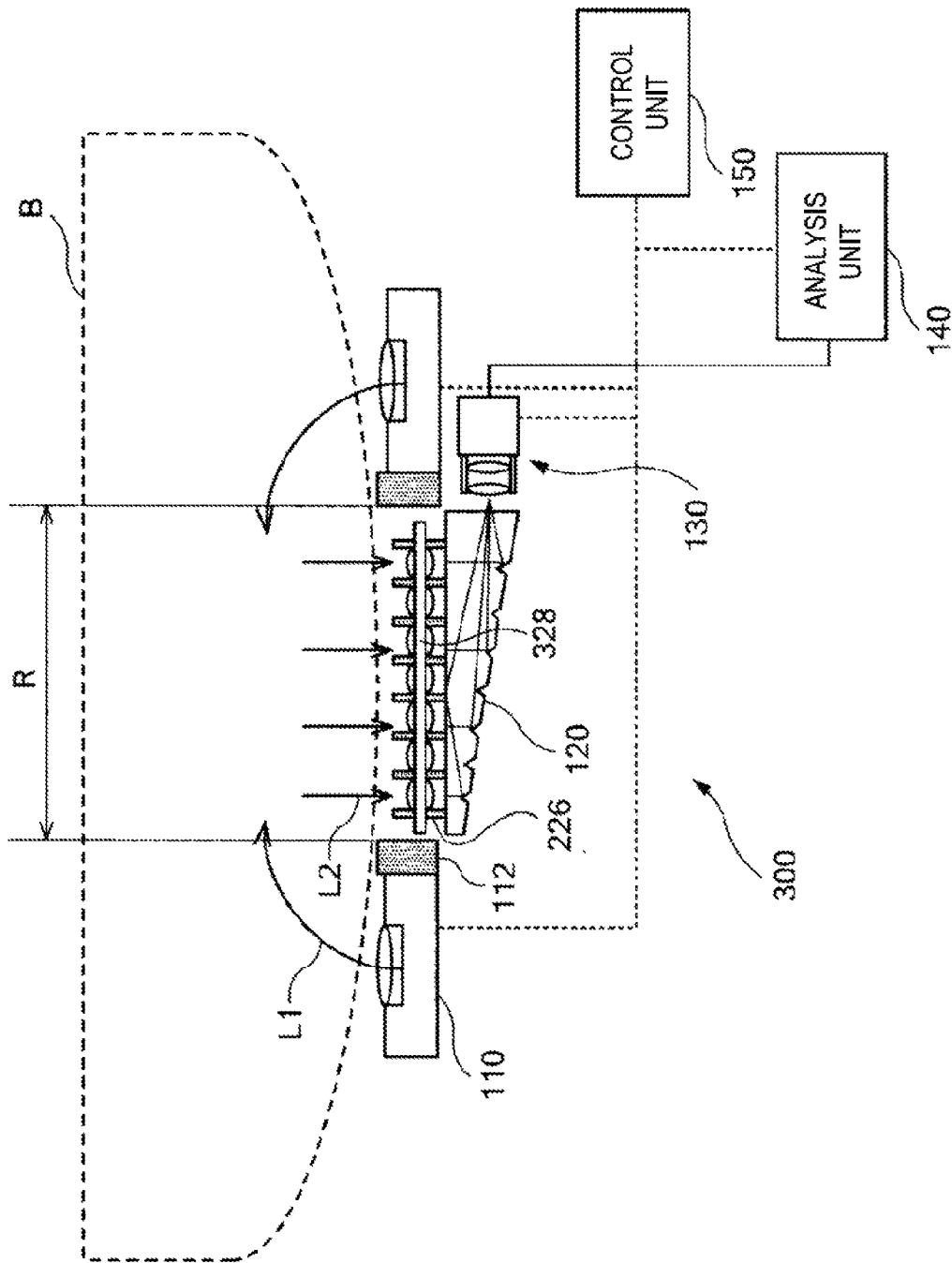
FIG. 7 is an illustration showing a configuration of a biometric device according to a third embodiment of the present disclosure.
Figure 8:
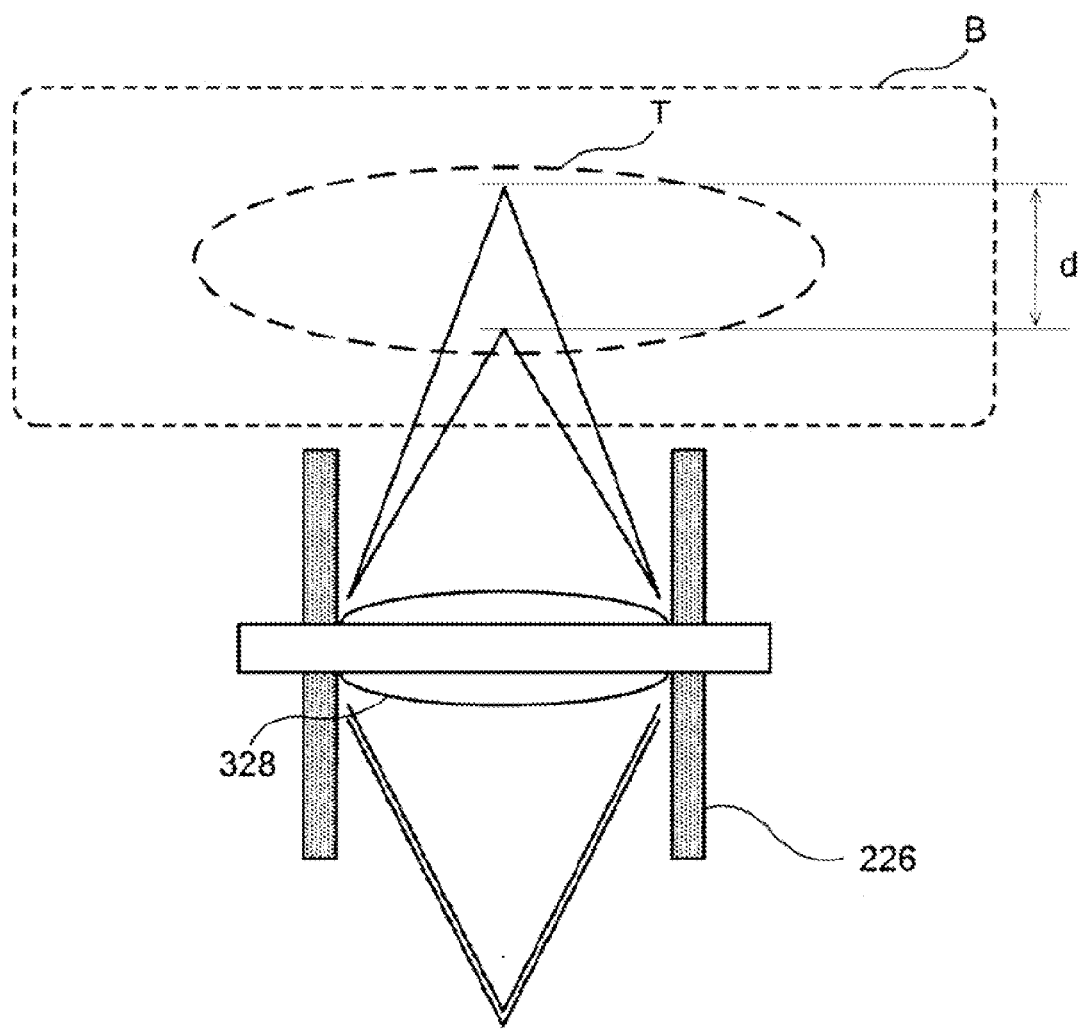
FIG. 8 is an illustration for describing depth of field of a microlens array.

A third embodiment of the present disclosure will be described hereinafter, with reference to FIG. 7 and FIG. 8. FIG. 7 is an illustration showing a configuration of a biometric device according to the third embodiment of the present disclosure. FIG. 8 is an illustration for describing depth of field of a microlens array.

With reference to FIG. 7, a biometric device 300 includes a light source unit 110, a light shield 112, a microprism array 120, a light-collecting light shield 226, a microlens array 328, a light-reception unit 130, an analysis unit 140, and a control unit 150. Note that of the aforementioned components, those other than the microlens array 328 can have a similar configuration to the second embodiment described above, and thus a detailed description will be omitted.

The microlens array 328 is a lens array of a plurality of small light-reception lenses having predetermined depth of field and being arranged in an array, and guides output light L2 entering the microprism array 120. As shown in FIG. 8, the depth of field d of the microlens array 328 corresponds to depth of a measurement target site T from a surface of an organism B, for example. If the measurement target site T is in a dermic layer of the organism B, the depth of field d may be set in a range in which a distance from the surface of the organism B is approximately 1 mm. This can limit a site of the organism B to which the output light L2 entering the microprism array 120 is emitted, thereby enabling improvement of precision in measurements using the output light L2.

2-4. Fourth Embodiment

Figure 9:
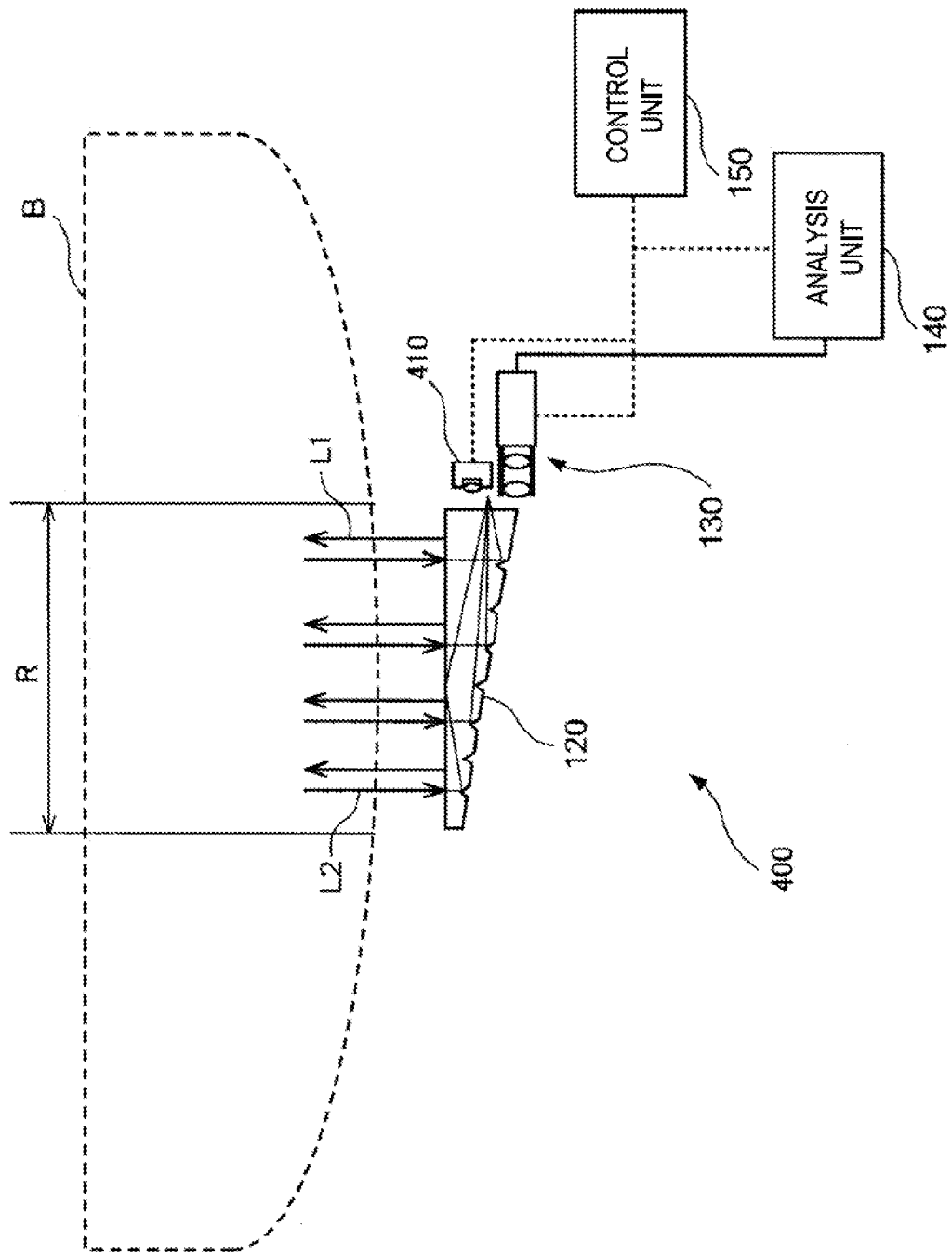
FIG. 9 is an illustration showing a configuration of a biometric device according to a fourth embodiment of the present disclosure.

A fourth embodiment of the present disclosure will be described hereinafter, with reference to FIG. 9 to FIG. 11. FIG. 9 is an illustration showing a configuration of a biometric device according to a fourth embodiment of the present disclosure.

Figure 10:
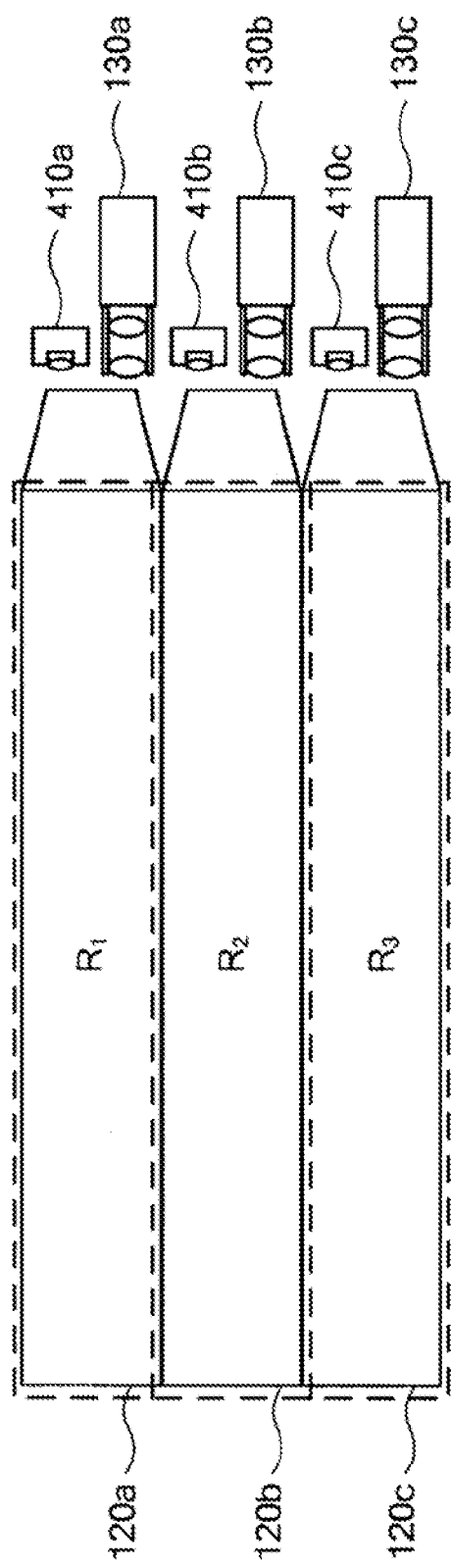
FIG. 10 is an illustration showing an example of dividing a region in the fourth embodiment of the present disclosure.

FIG. 10 is an illustration showing an example of dividing a region in the fourth embodiment of the present disclosure. FIG. 11 is an illustration showing the example of switching light reception and irradiation in the example of FIG. 10.

With reference to FIG. 9, a biometric device 400 includes a light source unit 410, a microprism array 120, a light-reception unit 130, an analysis unit 140, and a control unit 150. In addition, since the aforementioned components other than the light source unit 410 can have a similar configuration to the first embodiment described above, a detailed description will be omitted. In addition, these components can have a similar configuration to the second or third embodiment described above.

Although the light source unit 410 is a light source unit similar to the first embodiment described above, it differs from the light source unit 110 in that it is arranged corresponding to the light-reception unit 130. Specifically, the light source unit 410 is provided on the same side as the light-reception unit 130, with respect to the microprism array 120, and diffuses inspection light L1, which it applies, to an organism B by using the microprism array 120. Specifically, in this embodiment, the microprism array 120 acts as not only a light-collection unit but also a light-diffusion unit. According to such a configuration, the device configuration can be more simplified by arranging the light source unit 410 and the light-reception unit 130 in a compact manner.

FIG. 10 shows an example of dividing the region R in this embodiment, similar to FIG. 3 described above. In this example, light source units 410a to 410c for individually irradiating the sub-regions $R_1$ to $R_3$ with inspection light L1 are provided together with light-reception units 130a to 130c for individually receiving output light L2 collected in sub-regions $R_1$ to $R_3$. Specifically, in this example, the microprism array 120 is such divided that it diffuses the inspection light L1 to and collects the output light L2 from each sub-region $R_1$ to $R_3$ into which the region R is divided. The light source unit 410 and the light-reception unit 130 which correspond to each other perform irradiation of the inspection light L1 and light reception of the output light L2 alternatively, as in the following example.

Figure 11:
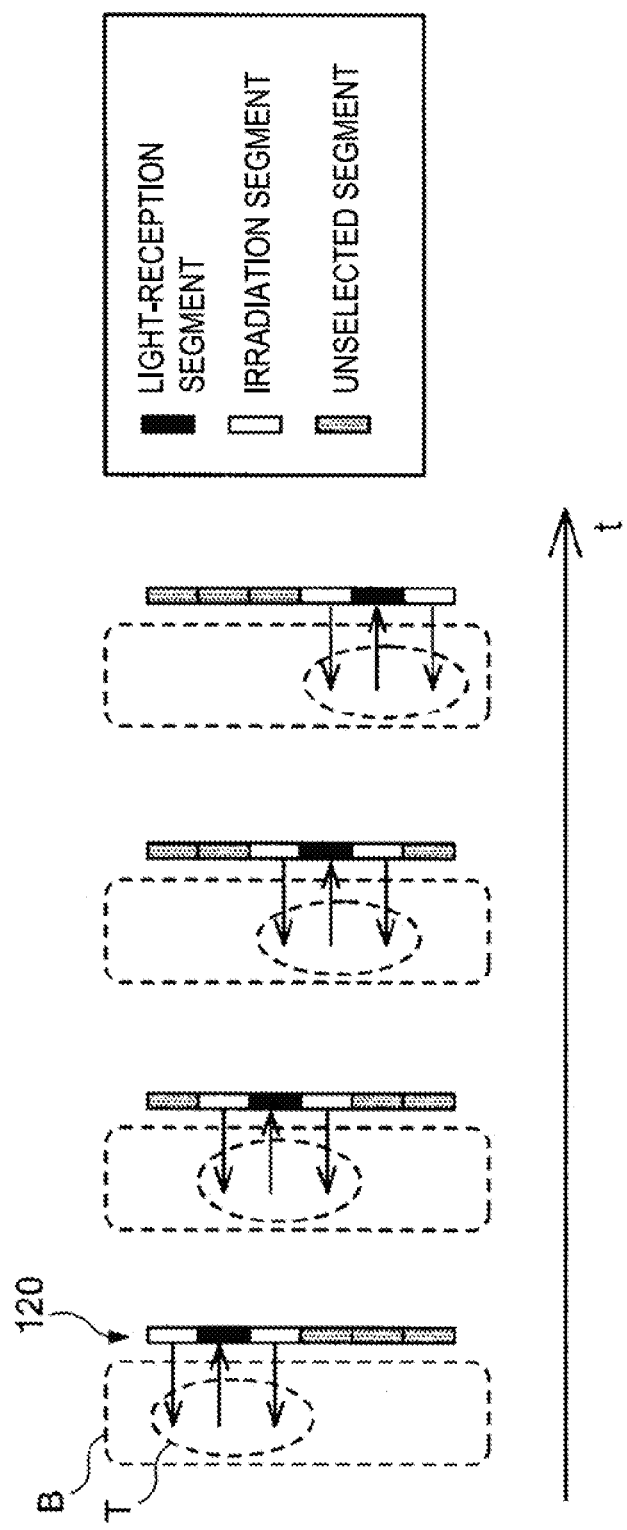
FIG. 11 is an illustration showing an example of switching between light reception and irradiation in the example of FIG. 10.

FIG. 11 shows an example of using the biometric device 400 as shown in FIG. 9 and FIG. 10 and performing measurements while sequentially changing a measurement target site T of the organism B. In the shown example, one light-reception segment and its neighboring two irradiation segments are selected from each segment of the microprism array 120. The measurement target site T can be sequentially changed by sequentially moving such light-reception segment and irradiation segments as time t progresses.

Note that here, the light-reception segment is a segment corresponding to a sub-region that can collect the output light L2 emitted from the organism B in accordance with the inspection light L1 applied from the irradiation segments. Therefore, it is not necessarily appropriate to make the neighboring segments of the light-reception segment an irradiation segment, as shown in the aforementioned example. For example, the larger depth of the measurement target site T from a surface of the organism B is, the farther an irradiation position of the inspection light L1 becomes from an exit position of the output light L2. Therefore, it is appropriate to adjust a distance between the light-reception segment and the irradiation segment, according to the depth of the measurement target site T from the surface of the organism B.

2-5. Fifth Embodiment

Figure 12:
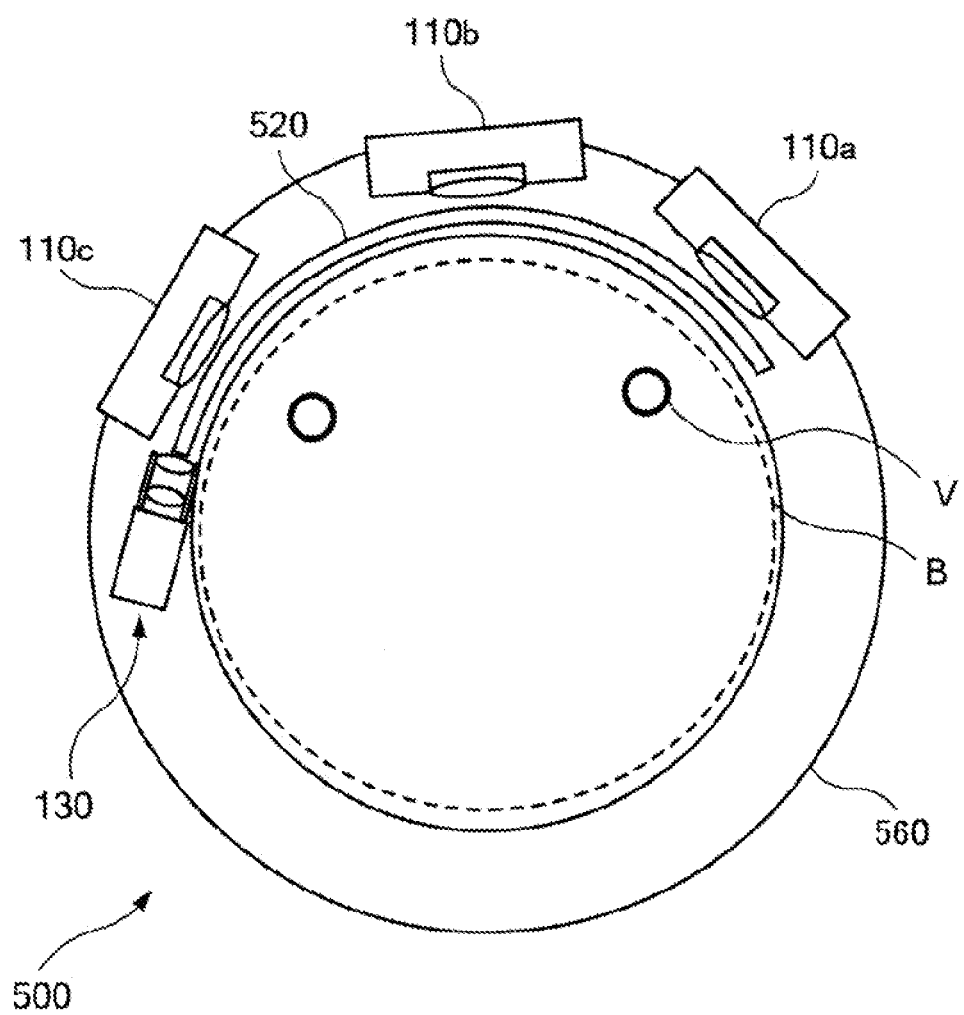
FIG. 12 is an illustration showing a configuration of a biometric device according to a fifth embodiment of the present disclosure.

A fifth embodiment of the present disclosure will be described hereinafter, with reference to FIG. 12. FIG. 12 is an illustration showing a configuration of a biometric device according to the fifth embodiment of the present disclosure.

With reference to FIG. 12, a biometric device 500 includes a light source unit 110, a microprism array 520, a light-reception unit 130, and a casing 560. An analysis unit and a control unit are not shown although they are included in the biometric device 500. In addition, since of the aforementioned components, those other than the microprism array 520 and the casing 560 can have a similar configuration to the first embodiment described above, a detailed description will be omitted. In addition, these components can have a similar configuration to any of the second to fourth embodiments described above.

The casing 560 is an annular casing into which an organism B can be inserted. Here, a site of the organism B to be inserted into the casing 560 is an arm or a finger, for example. Therefore, the biometric device 500 according to the embodiment may be a bracelet-like or ring-like measurement device, for example.

While the microprism array 520 is a light-collection unit similar to the microprism array 120 of the first embodiment described above, it differs from the microprism array 120 in that it is arranged along an inner periphery of the casing 560. Since a microprism array is formed of resin and the like, for example, it is easy to form the microprism array into a shape corresponding to a curved surface such as the inner periphery of the casing 560.

In this embodiment, the organism B is a part of a wrist, for example. In this case, the biometric device 500 may make an artery V inside the organism B a measurement target. In the biometric device 500, similar to the example shown in FIG. 4, the microprism array 520 is divided and the light-reception units 130 corresponding thereto are arranged. In addition, the light source units 110a to 110c are arranged respectively corresponding to sub-irradiated regions into which the region R is divided in a direction orthogonal to the dividing direction of the microprism array 520. This enables each of regions into which the region R is divided in a matrix to locally receive the output light L2. Therefore, as described above, even in a measurement of a pulse wave of the artery V in which selection of a measurement site is normally difficult, a site where optical waveform can be obtained can be automatically selected.

2-6. Sixth Embodiment

Figure 13:
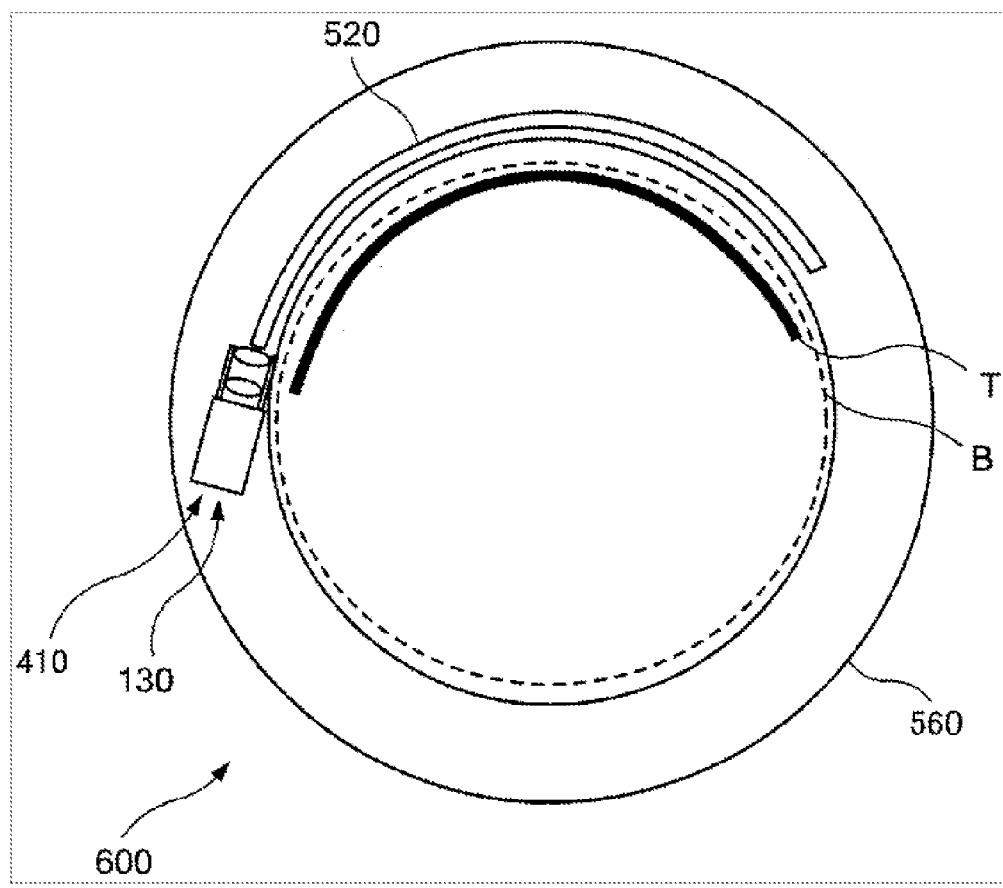
FIG. 13 is an illustration showing a configuration of a biometric device according to a sixth embodiment of the present disclosure.

A sixth embodiment of the present disclosure will be described hereinafter, with reference to FIG. 13. FIG. 13 is an illustration showing a configuration of a biometric device according to the sixth embodiment of the present disclosure.

With reference to FIG. 13, a biometric device 600 includes a light source unit 410, a microprism array 520, a light-reception unit 130, and a casing 560. An analysis unit and a control unit are not shown although they are included in the biometric device 600. While the biometric device 600 has a similar configuration to the biometric device 500 as described in the fifth embodiment above, it differs from the biometric device 500 in that the light source unit 410 is arranged, corresponding to the light-reception unit 130.

The biometric device 600 makes as a measurement target T a substance such as glucose or an advanced glycation end-products (AGEs: Advanced Glycation End-products) and the like lying under the skin of an organism B, which is an arm. In this case, the biometric device 600 irradiates a wide range on a surface of the organism B with excitation light as inspection light L1, and receives fluorescence light as output light L2. This can alleviate any effect of a singular point in measurement resulting from influence of skin hair, a bruise or a mole on the surface, or a blood vessel of an artery or a vein in the body, thereby improving sensitivity and stable student of measurements.

3. SUPPLEMENT

The embodiments of the present disclosure have been described above. In biometric devices according to the embodiments of the present disclosure, output light can be received from a wide region on a surface of an organism, without setting a distance between the surface of the organism and a light-reception unit like the biometric device according to the related art as shown in FIG. 1, for example, or without using a large-size light-reception device. In measurements of a subcutaneous material, for example, this can implement more freely and with high precision measurements with any effect of a singular point resulting from influence of skin hair, a bruise or a mole, or a blood vessel alleviated by collection of light from a wide region.

In addition, in a certain embodiment of the present disclosure, it is possible to divide a measurement target region and locally receive output light by dividing a light-collection unit and additionally distributing light source units. With this, even in a measurement in which a site suitable for the measurement is local, such as a measurement of a pulse wave of an arm, for example, a site suitable for a measurement can be easily detected.

In addition, in a certain embodiment of the present disclosure, use of a microprism array as a light-collection unit can make a shape of an overall measurement device flat. In addition, it becomes easy to collect output light from a curved surface in a bracelet-like or ring-like measurement device. In addition, what is used as a light-collection unit is not limited to a microprism array, and an optic fiber or a hologram lens, for example, may be used similarly.

(Hardware Configuration)

A hardware configuration of an information processor 900 capable of implementing a biometric device according to the embodiments of the present disclosure will be described hereinafter in detail with reference to FIG. 14. FIG. 14 is a block diagram for describing the hardware configuration of the information processor 900 according to the embodiments of the present disclosure.

The information processor 900 mainly includes a CPU 901, a ROM 903, and a RAM 905. In addition, the information processor 900 further includes a host bus 907, a bridge 909, an external bus 911, an interface 913, a sensor 914, an input device 915, an output device 917, a storage device 919, a drive 921, a connection port 923 and a communication device 925.

The CPU 901 acts as an arithmetic processing unit and a control device, and controls behavior in the information processor 900, in general, or a part thereof, according to various programs recorded in the ROM 903, the RAM 905, the storage device 919, or a removable recording medium 927. The ROM 903 stores a program or an arithmetic parameter and the like to be used by the CPU 901. The RAM 905 primarily stores a program to be used by the CPU 901 or a parameter which changes as appropriate in execution of the program, and the like. These are interconnected by the host bus 907 constituted of an internal bus such as a CPU bus and the like.

The hos bus 907 is connected with the external bus 911 such as a PCI (Peripheral Component Interconnect/Interface) bus by way of the bridge 909.

The sensor 914 is detecting means for detecting biological information unique to a user or various types of information to be used to acquire such biological information. This sensor 914 includes, for example, various imaging devices such as a CCD (Charge Coupled Device) or a CMOS (Complementary Metal Oxide Semiconductor) and the like. In addition, the sensor 914 may further have optics such as a lens to be used to image an organism site or a light source and the like. The sensor 914 may also be a microphone and the like for acquiring sound and the like. Note that in addition to those mentioned above, the sensor 914 may also include various measuring instruments such as a thermometer, an illuminance meter, a hygrometer, a speedometer, an accelerometer, and the like.

The input device 915 is an operational tool for a user to operate, such as a mouse, a keyboard, a touch panel, a button, a switch, and a lever, for example. The input device 915 may also be remote control means utilizing infrared rays or other electric wave or an externally connected device 929, such as a mobile phone or a PDA and the like, which responds to operation of the information processor 900. Furthermore, the input device 915 is constituted of an input control circuit and the like generating an input signal based on information which a user enters by using the aforementioned operational tool and outputting it to the CPU 901. By operating this input device 915, the user of the information processor 900 can input various types of data in the information processor 900 or give an instruction on processing operation.

The output device 917 is constituted of a device capable of visually or audibly informing the user of acquired information. Such a device includes a display device such as a CRT display unit, a liquid crystal display unit, a plasma display unit, an EL display unit, and a lamp and the like, or a voice output device such as a speaker and a headphone and the like, a printer unit, a mobile phone, a facsimile and the like. The output device 917 outputs a result obtained from various types of processing performed by the information processor 900, for example. Specifically, the display device displays the result obtained from the various types of processing performed by the information processor 900 in a text or an image. On the other hand, the audio output device converts an audio signal consisting of reproduced audio data or sound data and the like into an analog signal and outputs it.

The storage device 919 is a device for data storage configured as an example of a storage unit of the information processor 900. The storage device 919 is constituted of a magnetic storage unit device such as an HDD (Hard Disk Drive), a semiconductor storage device, an optical storage device, or a magneto-optical storage device and the like. This storage device 919 stores a program to be executed by the CPU 901 or various types of data, and various types of data acquired from the external, and the like.

The drive 921 is a reader-writer for a recording medium, and built in or externally mounted to the information processor 900. The drive 921 reads out information recorded in a mounted magnetic disk, optical disk or magneto-optical disk, or the removable recording medium 927 such as a semiconductor memory and the like, and outputs the information to the RAM 905. The drive 921 can also write a record in the mounted magnetic disk, optical disk or magneto-optical disk, or the removable recording medium 927 such as the semiconductor memory and the like. The removable recording medium 927 is, for example, a DVD medium, an HD-DVD medium, a Blu-ray medium and the like. The removable recording medium 927 may also be Compact Flash (Registered Trademark) (CompactFlash: CF), a flash memory or an SD memory card (Secure Digital memory card) and the like. In addition, the removable recording medium 927 may be an IC card (Integrated Circuit card) with a non-contact IC chip mounted or an electronic device and the like.

The connection port 923 is a port for directly connecting equipment to the information processor 900. By way of example, the connection port 923 includes a USB (Universal Serial Bus) port, an IEEE 1394 port, an SCSI (Small Computer System Interface) port and the like. As another example, the connection port 923 includes an RS-232C port, an optical audio terminal, an HDMI (High-Definition Multimedia Interface) port, and the like. By connecting the externally connected device 929 to this connection port 923, the information processor 900 directly acquires various types of data from the externally connected device 929 or provides the externally connected device 929 with various types of data.

The communication device 925 is a communication interface constituted of a communication device for connecting to a communication network 931, for example. The communication device 925 may be, for example, a communication card for a wired or wireless LAN (Local Area Network), Bluetooth (Registered Trademark), or WUSB (Wireless USB), and the like. In addition, the communication device 925 may be a router for optical communications, a router for ADSL (Asymmetric Digital Subscriber Line), or a modem for various types of communications and the like. This communication device 925 can send and receive a signal and the like to and from Internet or other communication devices, according to a predetermined protocol such as TCP/IP, for example. In addition, the communication network 931 connected to the communication device 925 is constituted of a network and the like connected by cable or wirelessly, and may be, for example, Internet, Home LAN, infrared communication, radio wave communication or satellite communication and the like.

As described above, one example of the hardware configuration which can implement capabilities of the information processor 900 according to the embodiments of the present disclosure has been shown. Respective components described above may be configured by the use of general-purpose members or may be configured by hardware specialized in the capabilities of the respective components. Therefore, it is possible to change a hardware configuration to utilize, as appropriate, depending on a technological level of when the embodiments are implemented.

The preferred embodiments of the present invention have been described above with reference to the accompanying drawings, whilst the technical scope of the present disclosure is not limited to the above examples, of course. It is obvious that a person skilled in the art may find various alterations and modifications within the technical ideas of the appended claims, and it should be understood that they will naturally come under the technical scope of the present invention.

Additionally, the present technology may also be configured as below.

(1)
A biometric device including:
a light source unit configured to irradiate an organism with inspection light;
a light-collection unit arranged facing a region on a surface of the organism and configured to spatially-integrally collect output light emitted from the region in accordance with the inspection light; and
a light-reception unit configured to receive the collected output light.

(2)
The biometric device according to (1),
wherein the light-collection unit is divided to collect the output light for each of a plurality of sub-regions into which the region is divided, and
wherein the light-reception unit individually receives the output light collected in each of the sub-regions.

(3)
The biometric device according to (2), wherein the light-reception unit receives the output light in a time division manner, the output light each being collected by the divided light-collection units.

(4)
The biometric device according to (2),
wherein the light-collection unit is divided in a first direction, and
wherein the light source unit is arranged corresponding to each of a plurality of sub-irradiated regions into which the region is divided in a second direction that is different from the first direction.

(5)
The biometric device according to (4), wherein the light source unit irradiates each of the sub-irradiated regions with the inspection light in a time division manner.

(6)
The biometric device according to any one of (1) to (3),
wherein the light source unit is arranged corresponding to the light-reception unit, and
wherein the light-collection unit also acts as a light-diffusion unit which diffuses to the organism the inspection light applied by the light source unit.

(7)
The biometric device according to (6),
wherein the light-collection unit is divided to diffuse the inspection light for each of a plurality of sub-regions into which the region is divided and collect the output light, and
wherein the light source unit and the light-reception unit alternatively perform irradiation of the inspection light and reception of the output light, for each of the sub-regions.

(8)
The biometric device according to any one of (1) to (7), further including:
an optical member configured to control directionality of light entering the light-collection unit.

(9)
The biometric device according to any one of (1) to (8), further including:
a lens array having a plurality of light-reception lenses arranged thereon in an array, the plurality of light-reception lenses having depth of field corresponding to depth of a body substance subject to measurement from the surface of the organism, and
wherein the output light entering the light-collection unit is guided by the lens array.

(10)
The biometric device according to any one of (1) to (9), further including:
an annular casing into which the organism is insertable, and
wherein the light-collection unit is arranged along an inner periphery of the casing.

(11)
The biometric device according to any one of (1) to (10), wherein a microprism array is used as the light-collection unit.

(12)
A biometric method including:
irradiating an organism with inspection light;
spatially-integrally collecting output light emitted from a region on a surface of the organism in accordance with the inspection light; and
receiving the collected output light.

(13)

A program for causing a computer included in a biometric device including a light source unit, a light-collection unit, and a light-reception unit to implement:

a function of controlling the light source unit; and a function of controlling the light-reception unit, the light source unit being configured to irradiate an organism with inspection light, the light-collection unit being arranged facing a region on a surface of the organism and being configured to spatially-integrally collect output light emitted from the region in accordance with the inspection light, the light-reception unit being configured to receive the collected output light.

(14)

A computer-readable recording medium having a program recorded thereon, the program causing a computer included in a biometric device including a light source unit, a light-collection unit, and a light-reception unit to implement a function of controlling the light source unit, and a function of controlling the light-reception unit, the light source unit being configured to irradiate an organism with inspection light, the light-collection unit being arranged facing a region on a surface of the organism and being configured to spatially-integrally collect output light emitted from the region in accordance with the inspection light, and the light-reception unit being configured to receive the collected output light.

(15)

A biometric device including:

a light source unit configured to irradiate an organism with inspection light;

a light-collection unit arranged facing a region on a surface of the organism and configured to spatially-integrally collect output light emitted from the region in accordance with the inspection light; and a light-reception unit configured to receive the collected output light, wherein the light-collection unit is divided to collect the output light for each of a plurality of sub-regions into which the region is divided, and wherein the light-reception unit receives the output light in a time division manner, the output light each being collected by the divided light-collection units.

REFERENCE SIGNS LIST 100 biometric device
110 light source unit
120 microprism array (light-collection unit)
130 light-reception unit
140 analysis unit
150 control unit

The invention claimed is:

1. A biometric device comprising:
at least one light source unit configured to irradiate a region of an organism with inspection light;
a light-collection unit configured to face a surface of the region of the organism and configured to cause output light emitted from the surface of the region to be spatially-integrally collected in accordance with the inspection light; and
at least one light-reception unit configured to receive the output light collected by the light-collection unit,
in which spatially-integrally collecting of the output light emitted from the region involves converging the output light into light having a cross-sectional size smaller than a size of the surface of the region,
in which the light-collection unit is configured to collect the output light emitted from each of a plurality of sub-regions into which the region is divided, and
in which the at least one light-reception unit includes a plurality of light-reception units to respectively receive the output light collected from the plurality of sub-regions by the light-collection unit in a sequential or time division manner such that each of the plurality of light-reception units is configured to correspond to a respective sub-region of the plurality of sub-regions and to individually receive the output light emitted from the respective sub-region in the sequential or time division manner.

2. The biometric device according to claim 1,
wherein the light-collection unit is divided in a first direction, and
wherein the at least one light source unit is arranged corresponding to each of a plurality of sub-irradiated regions into which the region is divided in a second direction that is different from the first direction.

3. The biometric device according to claim 1,
wherein the at least one light source unit is arranged corresponding to a given light-reception unit of the plurality of light-reception units, and
wherein the light-collection unit is configured to diffuse the inspection light applied by the light source unit to the organism.

4. The biometric device according to claim 3,
wherein the light-collection unit is configured to diffuse the inspection light emitted from each of the plurality of sub-regions, and
wherein the at least one light source unit and the given light-reception unit alternatively perform irradiation of the inspection light and reception of the output light, from each of the sub-regions.

5. The biometric device according to claim 1, further comprising:
an optical member configured to control directionality of light entering the light-collection unit.

6. The biometric device according to claim 1, further comprising:
a lens array having a plurality of light-reception lenses arranged thereon in an array, the plurality of light-reception lenses having depth of field corresponding to depth of a body substance subject to measurement from the surface of the organism, and
wherein the output light entering the light-collection unit is guided by the lens array.

7. The biometric device according to claim 1, further comprising:
an annular casing configured to enable the organism to be inserted thereinto, and
wherein the light-collection unit is arranged along an inner periphery of the casing.

8. The biometric device according to claim 1, wherein a microprism array is used as the light-collection unit.

9. A biometric method comprising:
irradiating a region of an organism with inspection light;
causing output light emitted from a surface of the region of the organism to be spatially-integrally collected at a light-collection unit in accordance with the inspection light; and
receiving the output light at light-reception unit,
in which spatially-integrally collecting of the output light emitted from the region involves converging the output light into light having a cross-sectional size smaller than a size of the surface of the region, in which region is divided into a plurality of sub-regions and in which the light-collection unit is configured to collect the output light emitted from each of the plurality of sub-regions, and in which the light-reception unit includes a plurality of sub-light-reception units to respectively receive the output light collected from the plurality of sub-regions in a sequential or time division manner such that each sub-reception-unit of the plurality of sub-light reception units is configured to correspond to a respective sub-region of the plurality of sub-regions and to individually receive the output light emitted from the respective sub-region in the sequential or time division manner.

10. A non-transitory computer-readable recording medium having a program recorded thereon, the program causing a computer included in a biometric device including at least one light source unit, a light-collection unit, and at least one light-reception unit to implement:

a function of controlling the at least one light source unit, and a function of controlling the at least one light-reception unit, the at least one light source unit being configured to irradiate a region of an organism with inspection light, the light-collection unit configured to face a surface of the region of the organism and being configured to cause output light emitted from the surface of the region to be spatially-integrally collected in accordance with the inspection light, and the at least one light-reception unit being configured to receive the output light collected by the light-collection unit, in which spatially-integrally collecting of the output light emitted from the region involves converging the output light into light having a cross-sectional size smaller than a size of the surface of the region, in which the light-collection unit is configured to collect the output light emitted from each of a plurality of sub-regions into which the region is divided, and in which the at least one light-reception unit includes a plurality of light-reception units to respectively receive the output light collected from the plurality of sub-regions by the light-collection unit in a sequential or time division manner such that each of the plurality of light-reception reception units is configured to correspond to a respective sub-region of the plurality of sub-regions and to individually receive the output light emitted from the respective sub-region in the sequential or time division manner.

11. A biometric device comprising:

at least one light source unit configured to irradiate a region of an organism with inspection light;

a light-collection unit configured to face a surface of the region of the organism and configured to cause output light emitted from the surface of the region to be spatially-integrally collected in accordance with the inspection light, in which spatially-integrally collecting of the output light emitted from the region involves converging the output light into light having a cross-sectional size smaller than a size of the surface of the region; and at least one light-reception unit configured to receive the output light collected by the light-collection unit, wherein the light-collection unit is configured to collect the output light emitted from each of a plurality of sub-regions into which the region is divided, and in which the at least one light-reception unit includes a plurality of light-reception units to respectively receive the output light collected from the plurality of sub-regions by the light-collection unit in a sequential or time division manner such that each of the plurality of light-reception units is configured to correspond to a respective sub-region of the plurality of sub-regions and to individually receive the output light emitted from the respective sub-region in the sequential or time division manner.

12. A biometric device comprising:

at least one light source unit configured to irradiate a region of an organism with inspection light;

a light-collection unit having a plurality of light-collection segments, each light-collection segment configured to face a surface of a sub-region of the region of the organism and configured to cause output light emitted therefrom to be spatially-integrally collected, in which spatially-integrally collecting of the output light involves converging the output light into light having a cross-sectional size smaller than a size of the surface of the respective sub-region, and in which the light-collection unit is configured to collect the output light emitted from each of a plurality of sub-regions into which the region is divided; and a plurality of light-reception units to respectively receive the output light collected from the plurality of sub-regions by the light-collection unit in a sequential or time division manner such that each of the plurality of light-reception units is configured to correspond to a respective sub-region of the plurality of sub-regions and to individually receive the output light emitted from the respective sub-region in the sequential or time division manner.

* * * * *